(12) United States Patent
Lee et al.

(10) Patent No.: US 6,448,415 B1
(45) Date of Patent: Sep. 10, 2002

(54) CHIRALITY CONVERSION METHOD IN LACTONE SUGAR COMPOUNDS

(75) Inventors: Sang Jo Lee, Taejeon (KR); Myung Joon Seo, Taejeon (KR); Nak Cheol Jeong, Taejeon (KR); Gun Cheol Kim, Taejeon (KR); Hyun Woung Hong, Taejeon (KR); Sul A Kim, Taejeon (KR)

(73) Assignee: Hanchem Co., Ltd., Taejeon (KR)

( * ) Notice: Subject to any disclaimer, the term of this patent is extended or adjusted under 35 U.S.C. 154(b) by 0 days.

(21) Appl. No.: 09/908,884

(22) Filed: Jul. 20, 2001

(30) Foreign Application Priority Data

Jul. 22, 2000 (KR) .............................................. 00-42115

(51) Int. Cl.[7] .............................................. C07D 493/00
(52) U.S. Cl. ....................................... 549/306; 548/283
(58) Field of Search ................................. 549/306, 283

*Primary Examiner*—Amelia Owens
(74) *Attorney, Agent, or Firm*—Birch, Stewart, Kolasch & Birch, LLP

(57) ABSTRACT

The present invention relates to a new process for effectively converting the chirality of 4- or 5-position carbon of a 1,4-lactone- or 1,5-lactone sugar compound which comprises reacting the lactone compound with secondary amine and sulfonyl group-containing compound. The compound of which chirality is converted according to the present invention can be advantageously used for preparing such expensive rare sugar compounds as L-ribose, D-talose, etc.

9 Claims, No Drawings

CHIRALITY CONVERSION METHOD IN LACTONE SUGAR COMPOUNDS

TECHNICAL FIELD

The present invention relates to a new process for effectively converting the chirality of 4- or 5-position carbon of a 1,4-lactone- or 1,5-lactone sugar compound which comprises reacting the lactone compound with a secondary amine and a sulfonyl group-containing compound. The compound of which chirality is converted according to the present invention can be advantageously used for preparing such expensive rare sugar compounds as L-ribose, D-talose, etc.

BACKGROUND ART

Since the rare sugar compounds including L-ribose are generally used as raw materials for food, cosmetics or medicines, lots of processes for preparing those compounds have been developed. Recently, as physiological functions of L-nucleosides have been gradually discovered with the support of genetic engineering, new medicines containing L-nucleoside are developed and thus, the demand for L-nucleosides are on the increase.

In particular, because the demand for L-ribose, the key intermediate for BW1263w94(Glaxo Wellcome) and L-FMAU (Bukwang & Triangle) that were developed as antiherpes and anti-hepatitis B, respectively, has been increasingly growing, many researchers in the field are interested in the development of an industrially applicable process for preparing the same(see: Nucleic acid & Nucleotide 18(2), 187(1999); JP 11/12294; WO 98/39347). In this regard, recently, a process for preparing L-ribose and rare sugar compounds has been developed using an enzyme controlling the chirality(WO 99/61648).

The existing process comprises the steps of opening the lactone ring taking advantage of the chemical property of lactones and converting the chirality of 4- and 5-position carbons in 1,4-lactone- or 1,5-lactone sugar compounds. Since the efficiency thereof is not good, however, today it is not used on an industrial scale, but restrictively used for the purpose of researches.

For example, a team of Japanese researchers has designed a process wherein a 1,5-lactone compound is reacted with a benzyloxyamine to produce an amide compound, which is then subjected to Mitsunobu reaction to convert the chirality of 5-position carbon in a comparatively high yield, as depicted in the following Reaction Scheme 1 (see: J. Am. Chem. Soc., 122, 2995(2000)):

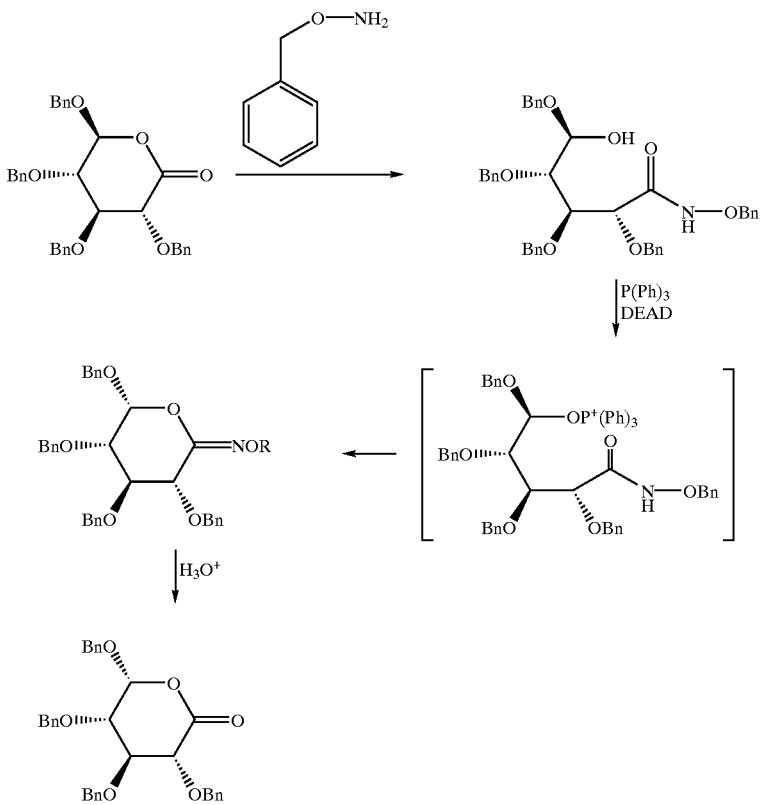

Reaction Scheme 1

This method provides a comparatively high reaction yield. However, the starting materials such as benzyloxyamine or DEAD are too expensive to afford; the reactant triphenylphosphine is not suitable for being used industrially; and work-up process is not easy due to some side reactions such as the formation of lactam compound by N-cyclization instead of the formation of lactone compound by O-cyclization. Therefore, this method is not appropriate for being utilized in an industrial production.

DISCLOSURE OF INVENTION

Thus, the present inventors have conducted extensive studies to effectively prepare such rare sugar compounds as L-ribose or D-talose by developing an efficient process for converting the chirality of 4- or 5-position carbon in a 1,4-lactone- or 1,5-lactone compound. As a result, we have found that such a purpose can be achieved by using secondary amine and sulfonyl group-containing compound as reactants, and then completed the present invention.

Therefore, the present invention is to provide a process for effectively converting the chirality of 4- or 5-position carbon in a lactone compound as represented by the following formula (1):

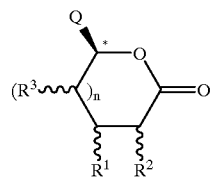
(1)

in which
n denotes a number of 0 or 1,
$R^1$, $R^2$ and $R^3$ independently of one another represent hydrogen, fluorine, straight-chain or branched $C_1$-$C_6$-alkoxy, $C_2$-$C_6$-carbonyloxy, benzoyloxy or benzyloxy, or two of them may combine to form isopropylidenedioxy or cyclohexylidenedioxy,
Q represents

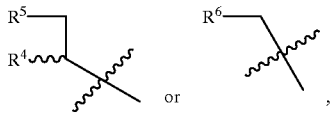

wherein $R^4$ and $R^5$ independently of one another represent hydrogen, straight-chain or branched $C_1$-$C_6$-alkoxy, $C_2$-$C_6$-carbonyloxy, benzoyloxy or benzyloxy, or may combine to form isopropylidenedioxy or cyclohexylidenedioxy, and $R^6$ represents straight-chain or branched $C_1$-$C_6$-alkoxy, $C_2$-$C_6$-carbonyloxy, benzoyloxy or benzyloxy.

BEST MODE FOR CARRYING OUT THE INVENTION

The present invention relates to a process for converting the chirality of 4- or 5-position carbon in a compound represented by the following formula (1):

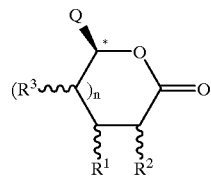
(1)

wherein n, $R^1$, $R^2$, $R^3$ and Q are defined as previously described,
which comprises reacting the compound of formula (1) with a secondary amine represented by the following (2):

(2)

wherein
R' and R" are identical or different and independently of one another represent straight-chain or branched $C_1$-$C_6$-alkyl, or together with the nitrogen atom to which they are attached may form 4- to 7-membered saturated hetero cycle,
and then reacting the resulting compound with a sulfonyl group-containing compound represented by the following formula (3):

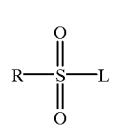
(3)

wherein
R represents straight-chain or branched $C_1$-$C_6$-alkyl, phenyl or tolyl, and
L represents a reactive leaving group, preferably halogen or

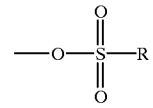

The above process according to the present invention is preferably carried out in a solvent. Any conventional organic solvent which does not adversely affect the reaction may be used, but preferably the one selected from a group consisting of ethyl acetate, methylene chloride, tetrahydrofuran, etc. is used. However, alcohols are not appropriate as the solvent. The reactant of the present invention, the secondary amine of the above formula (2), may also function as the solvent. Therefore, in such a case, the reaction may proceed smoothly without any additional solvent.

The reactant secondary amine of formula (2) is used in an excessive amount of 1 equivalent or more with respect to the lactone compound of formula (1). If excess amount is used, the reaction time may be cut down with no influence on the yield. As aforementioned, since the secondary amine may play a role of solvent or co-solvent in the process of the present invention, it may be used in an excess amount sufficient to dissolve the materials in the reaction system. Among the compound of formula (2), the preferred one to be used in the present invention is dimethylamine, diethylamine, diisopropylamine, pyrrolidine or piperidine.

The sulfonyl group-containing compound of formula (3) is used in an amount of 1 to 3 equivalents, preferably 2 equivalents, with respect to the compound of formula (1). When it is used in an amount of more than 3 equivalents, it is not easy to remove the compound of formula (3) that does not react during the work-up procedure. Among the compounds of formula (3) in the form of halide or anhydride, the preferred one is methanesulfonylchloride. In the step of reacting the compound of formula (3), triethylamine and dimethylaminopyridine may be used as the reaction-aid, and other aids having the same function may be used.

The reaction is carried out at temperatures ranging from −78 to 100° C., preferably of about 0° C.

The process according to the present invention can be explained based on the reaction mechanism as depicted in the following Reaction Scheme 2:

Reaction Scheme 2

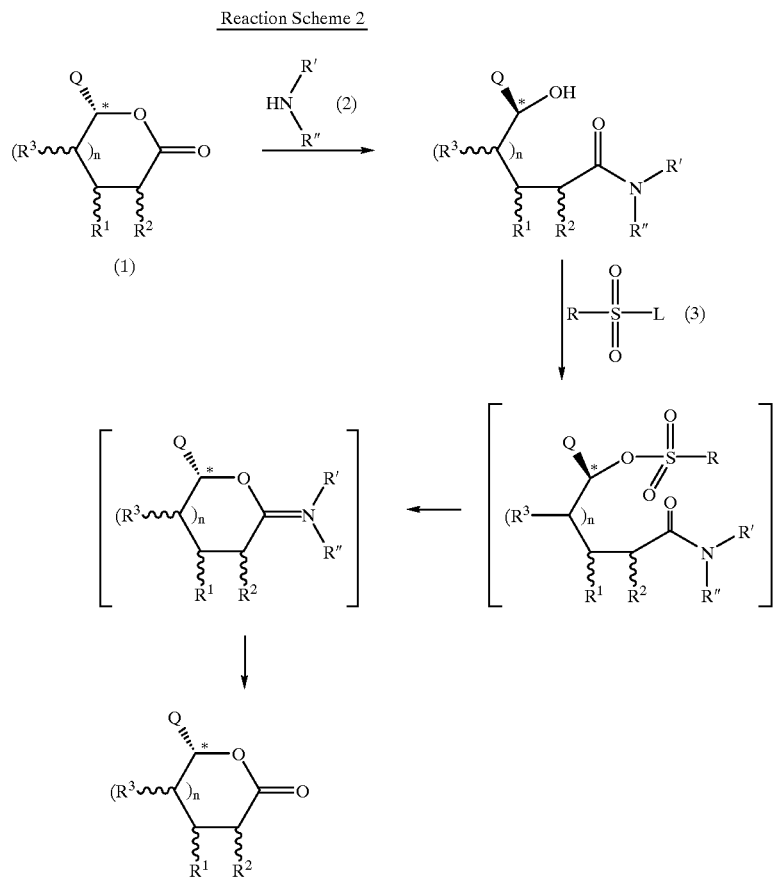

As explained in the above reaction scheme, the compound of formula (1) is reacted with the secondary amine to form an amide, which is then reacted with the sulfonyl group-containing compound of formula (3) to activate the hydroxy group. Thus activated compound is cyclized again to form a compound having the same structure as the starting compound, but the chirality of 4- or 5-position carbon of the lactone ring is converted. If the chirality of 4- or 5-position carbon of the starting compound is R-configuration, it is converted to S-configuration after the reaction and vice versa. That is, according to the present invention, the product compound does not have a newly introduced chirality but have a relatively converted chirality at 4- or 5-position carbon compared with the starting compound. The total reaction yield of this process is high, 85% or more.

After the intermediate of R-configuration is converted to that of S-configuration or vice versa according to the present invention, thus converted compound can be advantageously used for preparing such rare sugar compounds as L-ribose, D-talose, etc.

The present invention will be more specifically explained in the following examples. However, it should be understood that the following examples are intended to illustrate the present invention but not in any manner to limit the scope of the present invention.

EXAMPLES

Example 1

Conversion to 2,3:5,6-di-O-isopropylidene-D-talono-1,4-lactone

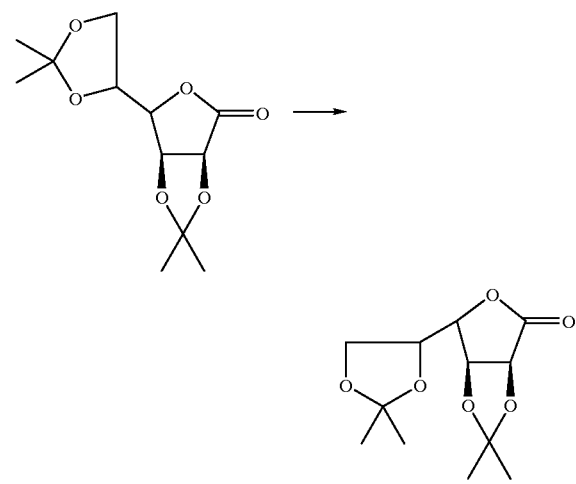

2,3:5,6-Di-O-isopropylidene-D-manono-1,4-lactone (16 g, 62 mmole) was dissolved in ethyl acetate (32 ml) and then piperidine (124 mmole) was added dropwise thereto at 0° C. After TLC revealed the completion of reaction, excess piperidine and solvent were removed by distillation under reduced pressure. The reactants were dissolved again by adding ethyl acetate (100 ml). Subsequently, triethylamine (Et₃N; 13.8 ml) and dimethylaminopyridine (100 mg) were added under nitrogen gas stream, and methanesulfonylchloride (9.6 ml, 124 mmole) was added dropwise at 0°C. After TLC revealed the completion of reaction, water was added to stop the reaction. The reaction mixture were extracted with ethyl acetate from the aqueous layer, dried over anhydrous magnesium sulfate, and concentrated under reduced pressure. The residue was purified by silica gel column chromatography (eluent: hexane/ethyl acetate=3/1, v/v) to give the title compound (13.6 g, Yield 85.0%) as a white solid.

Example 2

Conversion to 2,3:5,6-di-O-cyclohexylidene-D-talono-1,4-lactone

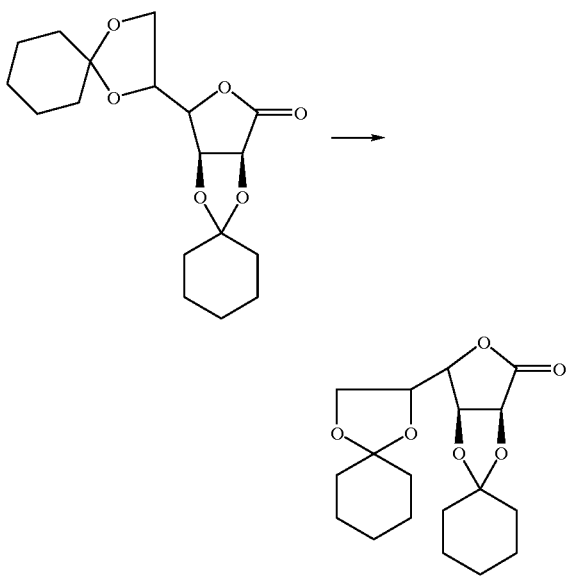

2,3:5,6-Di-O-cyclohexylidene-D-manono-1,4-lactone (10 g, 30 mmole) was dissolved in ethyl acetate (32 ml) and then piperidine (60 mmole) was added dropwise thereto at 0° C. After TLC revealed the completion of reaction, excess piperidine and solvent were removed by distillation under reduced pressure. The reactants were dissolved again by adding ethyl acetate (100 ml). Subsequently, triethylamine (Et₃N; 6.6 ml) and dimethylaminopyridine (50 mg) were added under nitrogen gas stream, and methanesulfonylchloride (4.6 ml, 60 mmole) was added dropwise at 0° C. After TLC revealed the completion of reaction, water was added to stop the reaction. The reaction mixture were extracted with ethyl acetate from the aqueous layer, dried over anhydrous magnesium sulfate, and concentrated under reduced pressure. The residue was purified by silica gel column chromatography (eluent: hexane/ethyl acetate=4/1, v/v) to give the title compound (8.7 g, Yield 87.2%) as a white solid.

Example 3

Conversion to 2,3:5,6-di-O-isopropylidene-L-allono-1,4-lactone

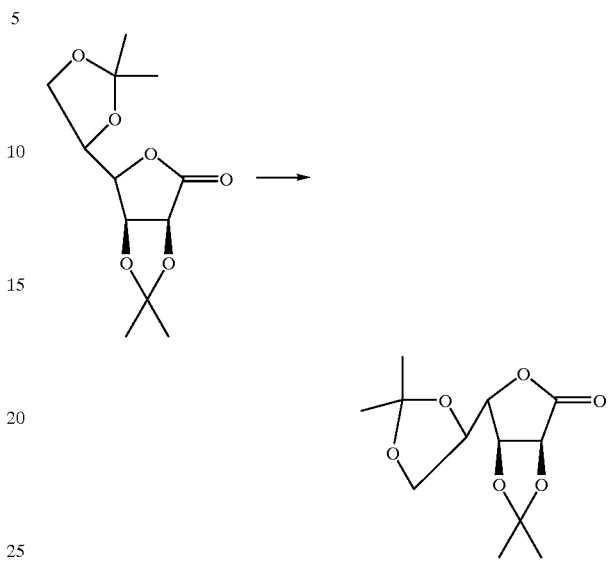

2,3:5,6-Di-O-isopropylidene-L-gluono-1,4-lactone (13.3 g, 51 mmole) was dissolved in ethyl acetate (27 ml) and then diisopropylamine (102 mmole) was added dropwise thereto at 0° C. After TLC revealed the completion of reaction, excess diisopropylamine and solvent were removed by distillation under reduced pressure. The reactants were dissolved again by adding ethyl acetate (83 ml). Subsequently, triethylamine (Et₃N; 11.5 ml) and dimethylaminopyridine (100 mg) were added under nitrogen gas stream, and methanesulfonylchloride (7.9 ml, 102 mmole) was added dropwise at 0° C. After TLC revealed the completion of reaction, water was added to stop the reaction. The reaction mixture were extracted with ethyl acetate from the aqueous layer, dried over anhydrous magnesium sulfate, and concentrated under reduced pressure. The residue was purified by silica gel column chromatography (eluent: hexane/ethyl acetate=3/1, v/v) to give the title compound (11.3 g, Yield 85.0%) as a white solid.

Example 4

Conversion to 2,3:5,6-di-O-cyclohexylidene-L-allono-1,4-lactone

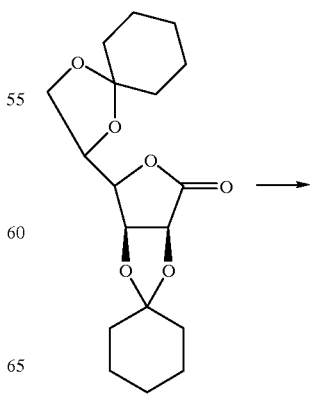

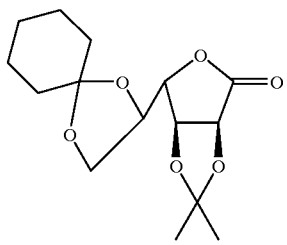

2,3:5,6-Di-O-cyclohexylidene-L-gluono-1,4-lactone (12.3 g, 36.4 mmole) was dissolved in ethyl acetate (38 ml) and then piperidine (73 mmole) was added dropwise thereto at 0° C. After TLC revealed the completion of reaction, excess piperidine and solvent were removed by distillation under reduced pressure. The reactants were dissolved again by adding ethyl acetate (120 ml). Subsequently, triethylamine ($Et_3N$; 8.0 ml) and dimethylaminopyridine (100 mg) were added under nitrogen gas stream, and methanesulfonylchloride (5.6 ml, 72 mmole) was added dropwise at 0° C. After TLC revealed the completion of reaction, water was added to stop the reaction. The reaction mixture were extracted with ethyl acetate from the aqueous layer, dried over anhydrous magnesium sulfate, and concentrated under reduced pressure. The residue was purified by silica gel column chromatography (eluent: hexane/ethyl acetate=4/1, v/v) to give the title compound (10.5 g, Yield 86.0%) as a white solid.

Example 5

Conversion to 2,3,5-tri-O-benzyl-L-xylono-1,4-lactone

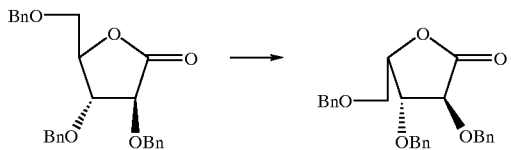

2,3,5-Tri-O-benzyl-D-arabinono-1,4-lactone (10 g, 23.9 mmole) was dissolved in ethyl acetate (20 ml) and then piperidine (48 mmole) was added dropwise thereto at 0° C. After TLC revealed the completion of reaction, excess piperidine and solvent were removed by distillation under reduced pressure. The reactants were dissolved again by adding ethyl acetate (50 ml). Subsequently, triethylamine ($Et_3N$; 5.3 ml) and dimethylaminopyridine (50 mg) were added under nitrogen gas stream, and methanesulfonylchloride (3.7 ml, 47.6 mmole) was added dropwise at 0° C. After TLC revealed the completion of reaction, water was added to stop the reaction. The reaction mixture were extracted with ethyl acetate from the aqueous layer, dried over anhydrous magnesium sulfate, and concentrated under reduced pressure. The residue was purified by silica gel column chromatography (eluent: hexane/ethyl acetate=4/1, v/v) to give the title compound (8.5 g, Yield 85.0%) as a white solid.

Example 6

Conversion to 5-O-benzyl-2,3-O-isopropylidene-L-lyxono-1,4-lactone

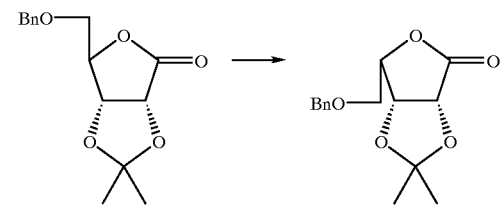

5-O-benzyl-2,3-O-isopropylidene-D-ribono-1,4-lactone (10 g, 36.0 mmole) was dissolved in ethyl acetate (20 ml) and then piperidine (72 mmole) was added dropwise thereto at 0° C. After TLC revealed the completion of reaction, excess piperidine and solvent were removed by distillation under reduced pressure. The reactants were dissolved again by adding ethyl acetate (70 ml). Subsequently, triethylamine ($Et_3N$; 8 ml) and dimethylaminopyridine (50 mg) were added under nitrogen gas stream, and methanesulfonylchloride (5.6 ml, 72 mmole) was added dropwise at 0° C. After TLC revealed the completion of reaction, water was added to stop the reaction. The reaction mixture were extracted with ethyl acetate from the aqueous layer, dried over anhydrous magnesium sulfate, and concentrated under reduced pressure. The residue was purified by silica gel column chromatography (eluent: hexane/ethyl acetate=4/1, v/v) to give the title compound (8.6 g, Yield 86.0%) as a white solid.

Example 7

Conversion to 2-deoxy-3,5-O-dibenzyl-L-lyxono-1,4-lactone

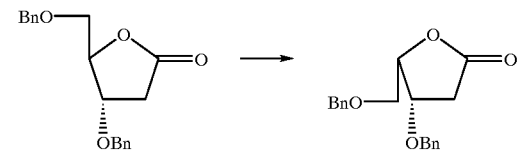

2-Deoxy-3,5-O-dibenzyl-D-ribono-1,4-lactone (10 g, 32 mmole) was dissolved in ethyl acetate (20 ml) and then piperidine (64 mmole) was added dropwise thereto at 0° C. After TLC revealed the completion of reaction, excess piperidine and solvent were removed by distillation under reduced pressure. The reactants were dissolved again by adding ethyl acetate (50 ml). Subsequently, triethylamine ($Et_3N$; 7.1 ml) and dimethylaminopyridine (50 mg) were added under nitrogen gas stream, and methanesulfonylchloride (5.0 ml, 64 mmole) was added dropwise at 0° C. After TLC revealed the completion of reaction, water was added to stop the reaction. The reaction mixture were extracted with ethyl acetate from the aqueous layer, dried over anhydrous magnesium sulfate, and concentrated under reduced pressure. The residue was purified by silica gel column chromatography (eluent: hexane/ethyl acetate=4/1, v/v) to give the title compound (8.7 g, Yield 87.0%) as a white solid.

Example 8

Conversion to 2,3:4,6-tetra-O-benzyl-L-idono-1,5-lactone

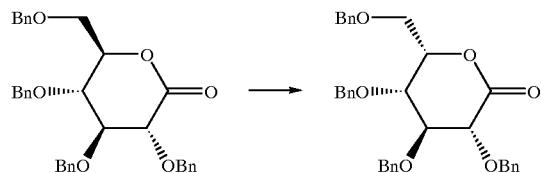

2,3:4,6-Tetra-O-benzyl-D-glucono-1,4-lactone (10 g, 18.5 mmole) was dissolved in ethyl acetate (20 ml) and then piperidine (37 mmole) was added dropwise thereto at 0° C. After TLC revealed the completion of reaction, excess piperidine and solvent were removed by distillation under reduced pressure. The reactants were dissolved again by adding ethyl acetate (30 ml). Subsequently, triethylamine ($Et_3N$; 4.2 ml) and dimethylaminopyridine (50 mg) were added under nitrogen gas stream, and methanesulfonylchloride (2.9 ml, 37 mmole) was added dropwise at 0° C. After TLC revealed the completion of reaction, water was added to stop the reaction. The reaction mixture were extracted with ethyl acetate from the aqueous layer, dried over anhydrous magnesium sulfate, and concentrated under reduced pressure. The residue was purified by silica gel column chromatography (eluent: hexane/ethyl acetate=4/1, v/v) to give the title compound (8.8 g, Yield 88.0%) as a white solid.

INDUSTRIAL APPLICABILITY

As explained above, according to the new process provided by the present invention, the chirality of 4- or 5-position carbon in the compound of formula (1) can be efficiently converted, whereby the intermediates useful for preparing such rare sugar compounds as L-ribose or D-talose can be effectively obtained.

What is claimed is:

1. A process for converting the chirality of 4- or 5-position carbon in a compound represented by the following formula (1):

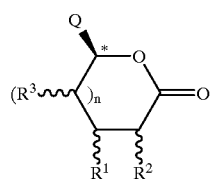

(1)

wherein n denotes a number of 0 or 1, $R^1$, $R^2$ and $R^3$ independently of one another represent hydrogen, fluorine, straight-chain or branched $C_1$-$C_6$-alkoxy, $C_2$-$C_6$-carbonyloxy, benzoyloxy or benzyloxy, or two of them may combine to form isopropylidenedioxy or cyclohexylidenedioxy, Q represents

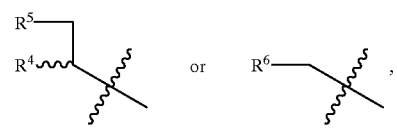

$R^4$ and $R^5$ independently of one another represent hydrogen, straight-chain or branched $C_1$-$C_6$-alkoxy, $C_2$-$C_6$-carbonyloxy, benzoyloxy or benzyloxy, or may combine to form isopropylidenedioxy or cyclohexylidenedioxy, and $R^6$ represents straight-chain or branched $C_1$-$C_6$-alkoxy, $C_2$-$C_6$-carbonyloxy, benzoyloxy or benzyloxy, which comprises reacting the compound of formula (1) with a secondary amine represented by the following formula (2):

(2)

wherein

R' and R" are identical or different and independently of one another represent straight-chain or branched $C_1$-$C_6$-alkyl, or together with the nitrogen atom to which they are attached may form 4- to 7-membered saturated hetero cycle, and then reacting the resulting compound with a sulfonyl group- containing compound represented by the following formula (3):

(3)

wherein

R represents straight-chain or branched $C_1$-$C_6$-alkyl, phenyl or tolyl, and

L represents halogen or

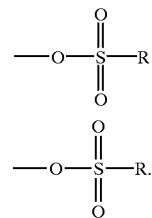

2. The process of claim 1 wherein the reaction is carried out in one or more solvents selected from a group consisting of ethyl acetate, methylene chloride and tetrahydrofuran.

3. The process of claim 1 wherein the secondary amine of formula (2) is one or more selected from a group consisting of dimethylamine, diethylamine, diisopropylamine, pyrrolidine and piperidine.

4. The process of claim 1 wherein the sulfonyl group-containing compound of formula (3) is methanesulfonylchloride.

5. The process of claim 1 wherein triethylamine and dimethylamino-pyridine are used as reaction aid together with methanesulfonylchloride.

6. The process of claim 1 wherein the reaction is carried out at temperatures ranging from −78 to 100° C.

7. The process of claim 2 wherein triethylamine and dimethylamino-pyridine are used as reaction aid together with methanesulfonylchloride.

8. The process of claim 3 wherein triethylamine and dimethylamino-pyridine are used as reaction aid together with methanesulfonylchloride.

9. The process of claim 4 wherein triethylamine and dimethylamino-pyridine are used as reaction aid together with methanesulfonylchloride.

* * * * *